(12) United States Patent
Moseley et al.

(10) Patent No.: US 12,127,954 B2
(45) Date of Patent: Oct. 29, 2024

(54) IMPLANT REMOVAL TOOL

(71) Applicant: Spinal Simplicity, LLC, Overland Park, KS (US)

(72) Inventors: Todd Moseley, Olathe, KS (US); Adam Frock, Lenexa, KS (US); Melissa Frock, Lenexa, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 18/313,528

(22) Filed: May 8, 2023

(65) Prior Publication Data

US 2023/0380991 A1 Nov. 30, 2023

Related U.S. Application Data

(63) Continuation of application No. 17/825,939, filed on May 26, 2022, now Pat. No. 11,679,005.

(51) Int. Cl.
*A61F 2/46* (2006.01)

(52) U.S. Cl.
CPC ..... *A61F 2/4611* (2013.01); *A61F 2002/4619* (2013.01); *A61F 2002/4629* (2013.01)

(58) Field of Classification Search
CPC ...... A61F 2002/4619; A61F 2002/4629; A61F 2/4657; A61F 2/4684; A61B 17/8875; A61B 17/8877; A61B 17/888; A61B 17/8883; A61B 17/8886; A61B 17/8888; A61B 17/8891; A61B 17/8894
See application file for complete search history.

(56) References Cited

U.S. PATENT DOCUMENTS

| | | | | |
|---|---|---|---|---|
| 5,375,956 A | * | 12/1994 | Pennig | A61B 17/8605 411/397 |
| 6,033,405 A | * | 3/2000 | Winslow | A61F 2/4611 606/86 R |
| 7,140,087 B1 | * | 11/2006 | Giltner | B25B 27/18 81/53.2 |
| 2011/0313457 A1 | * | 12/2011 | Reglos | A61B 17/7065 606/279 |
| 2012/0197311 A1 | * | 8/2012 | Kirschman | A61B 17/7098 606/104 |
| 2013/0072986 A1 | * | 3/2013 | Robinson | A61B 17/8891 606/279 |
| 2013/0125714 A1 | * | 5/2013 | Dahners | B25B 15/007 411/407 |
| 2015/0134014 A1 | * | 5/2015 | Palmer | A61B 17/8875 606/304 |

* cited by examiner

*Primary Examiner* — Matthew J Lawson
(74) *Attorney, Agent, or Firm* — Erise IP, P.A.

(57) ABSTRACT

An implant removal tool for use in removing an expandable spinal implant device from a patient and a method of use. The tool includes a shaft having a distal end with a plurality of tabs and a central bore having a threaded section with an internal threaded wall. The plurality of tabs may include two curved tabs having blunt distal ends for cooperating with an implant. The threaded section is configured to receive a threaded shaft of an implant and lock the implant thereon for removal.

20 Claims, 4 Drawing Sheets

IMPLANT REMOVAL TOOL

CROSS-REFERENCE TO RELATED APPLICATIONS

This patent application is a continuation application claiming priority benefit, with regard to all common subject matter, of U.S. patent application Ser. No. 17/825,939, filed May 26, 2022, and entitled "IMPLANT REMOVAL TOOL." The above-referenced application is hereby incorporated by reference in its entirety into the present application.

BACKGROUND

1. Field

Embodiments of the invention relate to instruments for removing implanted surgical devices. More specifically, embodiments of the invention relate to a tool for easily removing an expandable spinal implant.

2. Related Art

The spine consists of a column of twenty-four vertebrae that extend from the skull to the hips. Discs of soft tissue are disposed between adjacent vertebrae. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness, and/or loss of balance. These symptoms often increase after walking or standing for a period of time.

There are a number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, a spinal implant or spacer device is positioned behind the spinal cord or nerves and between the interspinous processes that protrude from the vertebrae in the lower back. Interspinous interlaminar fusion devices may be used for the temporary fixation of the thoracic, lumbar, and sacral spine while waiting for bony fusion to occur.

Examples of particularly useful interspinous process implant and fusion devices are disclosed in commonly assigned U.S. Pat. Nos. 9,861,399, 8,945,184; 9,314,276, 9,907,581, 9,757,164, and U.S. patent application Ser. No. 16/998,771, the disclosures of which are all incorporated herein by reference in their entirety. Such implants may be designed for attachment to the posterior non-cervical spine at the spinous process through bilateral locking plates.

Sometimes an implanted spinal device fails and needs to be removed and/or replaced. In such cases, a surgeon must perform a surgical procedure to remove the implant before a new device may be inserted.

The instant invention provides an improvement over prior devices by providing a combined instrument for both preparing the implant to be removed and for actually removing the implant from the patient site. Spinal implants typically have a closed configuration for insertion and removal and an expanded open configuration for in situ use. To prepare an implant to be removed, a surgeon must typically perform a two-step process, which includes first moving the implant into the closed configuration and then removing the implant from the implanted location. Commonly two separate tools are required for this two-step process.

The combined removal tool of the present invention will advantageously reduce the number of additional tools necessary for the surgical procedure, thereby making implantation safer and easier. Additionally, the device of the present invention adequately anchors to the implant to ensure safe and complete removal from the patient.

SUMMARY

Embodiments of the invention solve the above-mentioned problems by providing a surgical instrument and method for performing minimally invasive spinal surgery and removing an implanted device.

In some aspects, the techniques described herein relate to a surgical tool for removing a surgical implant including: a handle; a shaft having a distal end with a first wall thickness; the distal end including a central bore, the central bore having a proximal region including an internal threaded wall, wherein the internal threaded wall is configured to receive a threaded shaft of an implant to be removed; and a plurality of tabs extending from a distalmost region, the plurality of tabs having a second wall thickness greater than the first wall thickness such that the plurality of tabs extend radially into the central bore.

In some aspects, the techniques described herein relate to a surgical tool, wherein the central bore includes: a proximal region having a first diameter; an intermediate region having a second diameter; and the distalmost region having a third diameter, wherein the first diameter is smaller than the second diameter, and the second diameter is smaller than the third diameter.

In some aspects, the techniques described herein relate to a surgical tool, wherein the third diameter is about 3.4 mm to about 4.0 mm.

In some aspects, the techniques described herein relate to a surgical tool, wherein the plurality of tabs includes two curved tabs each having a blunt distal end.

In some aspects, the techniques described herein relate to a surgical tool, wherein the plurality of tabs includes two tabs each having a width around a circumference of about 2.3 mm to about 2.9 mm.

In some aspects, the techniques described herein relate to a surgical tool, wherein the plurality of tabs each extend longitudinally a distance of about 3 mm from the distalmost region.

In some aspects, the techniques described herein relate to a surgical tool, wherein the plurality of tabs each span an arc of about 40 degrees to about 60 degrees.

In some aspects, the techniques described herein relate to a surgical tool, wherein the internal threaded wall includes a plurality of helical threads having a pitch of about 0.6 mm.

In some aspects, the techniques described herein relate to a method of removing a surgical implant from a patient including: providing a removal tool including: a handle; a shaft having a distal end with a first wall thickness; the distal end including a central bore, the central bore having a proximal region including an internal threaded wall; and a plurality of tabs extending from a distalmost region, the plurality of tabs having a second wall thickness greater than the first wall thickness such that the plurality of tabs extend radially into the central bore; engaging the removal tool with an implant; and rotating the removal tool to lock the implant onto the distal end of the shaft.

In some aspects, the techniques described herein relate to a method, wherein engaging the removal tool with the implant includes: inserting the plurality of tabs into a proximal face of the implant.

In some aspects, the techniques described herein relate to a method, further including receiving the plurality of tabs in indented portions of a collar on the implant.

In some aspects, the techniques described herein relate to a method, wherein engaging the removal tool with the implant includes: inserting the distal end of the shaft into a circumferential gap on a proximal face of the implant.

In some aspects, the techniques described herein relate to a method, further including: rotating the removal tool counterclockwise to engage a threaded shaft of the implant with the internal threaded wall.

In some aspects, the techniques described herein relate to a method, wherein rotating the removal tool counterclockwise further rotates the threaded shaft of the implant to close a plurality of wings of the implant.

In some aspects, the techniques described herein relate to a method, further including: after locking the implant onto the distal end of the shaft, withdrawing the removal tool from a patient's body to remove the implant.

In some aspects, the techniques described herein relate to a surgical implant removal device including: a shaft having a proximal end and distal end with a first wall thickness; the distal end including a central bore with a diameter of about 3.4 mm to about 4.0 mm; the central bore having a plurality of threads on an interior at a distalmost end; two curved tabs extending from the distalmost end, the two curved tabs having a blunt distal end, and the two curved tabs configured to cooperate with an implant for removal from a target site.

In some aspects, the techniques described herein relate to a surgical implant removal device, wherein the plurality of threads are configured to cooperate with a threaded shaft of the implant.

In some aspects, the techniques described herein relate to a surgical implant removal device, wherein the central bore is sized to receive the threaded shaft of the implant.

In some aspects, the techniques described herein relate to a surgical implant removal device, wherein the two curved tabs each extend around a circumference a distance of about 2-3 mm and extend a length from the distalmost end of about 3-4 mm.

In some aspects, the techniques described herein relate to a surgical implant removal device, wherein the two curved tabs have a second wall thickness greater than the first wall thickness such that the two curved tabs extend radially into the central bore.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
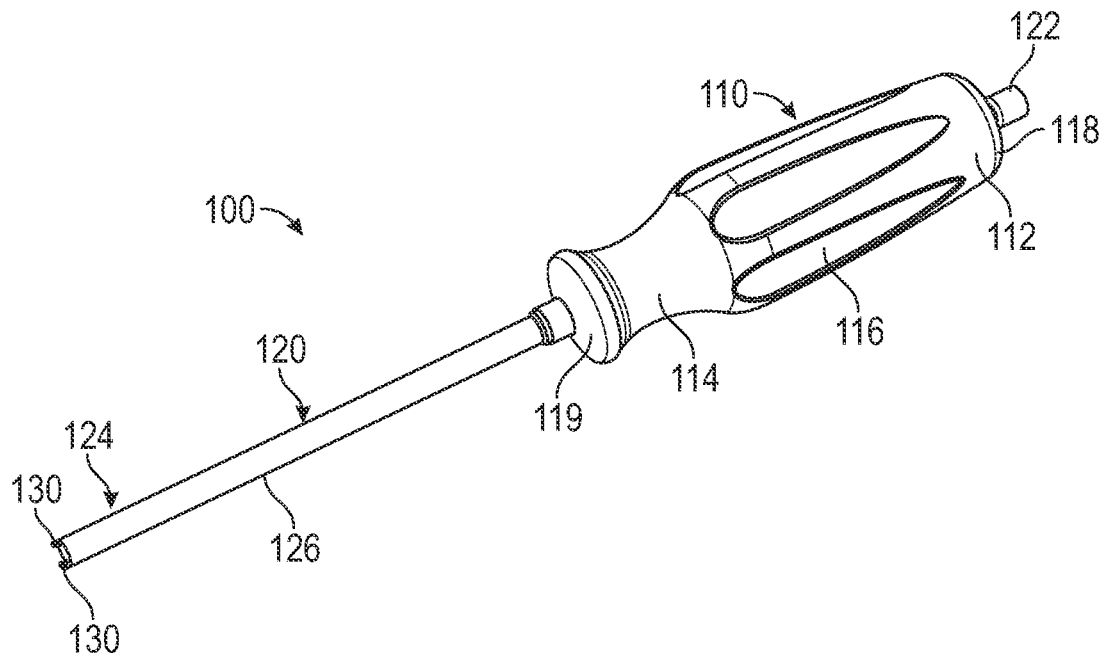
FIG. 1 shows a perspective view of a first embodiment of a multi-functional implant removal tool.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the technology can include a variety of combinations and/or integrations of the embodiments described herein.

Embodiments of the invention are directed to an implant removal tool for use in removing an expandable spinal implant device.

FIG. 1 illustrates a perspective view of a multi-functional implant removal tool 100 of one embodiment. In some embodiments, tool 100 includes handle 110 and shaft 120. Handle 110 includes proximal handle portion 112 and distal handle portion 114. Proximal handle portion 112 may include indentations 116 to aid in gripping by a user. Indentations 116 may be substantially teardrop-shaped in some embodiments, as seen in FIG. 1. Distal handle portion 114 may be shaped to have an hourglass form, such that a central portion thereof has a smaller diameter than both the proximal portion and the distal portion, to aid in gripping by a user. Handle 110 may be solid with a central lumen 115 therethrough for receiving the shaft 120 therein. In some embodiments, handle 110 may be hollow in at least some portions.

Figure 2:
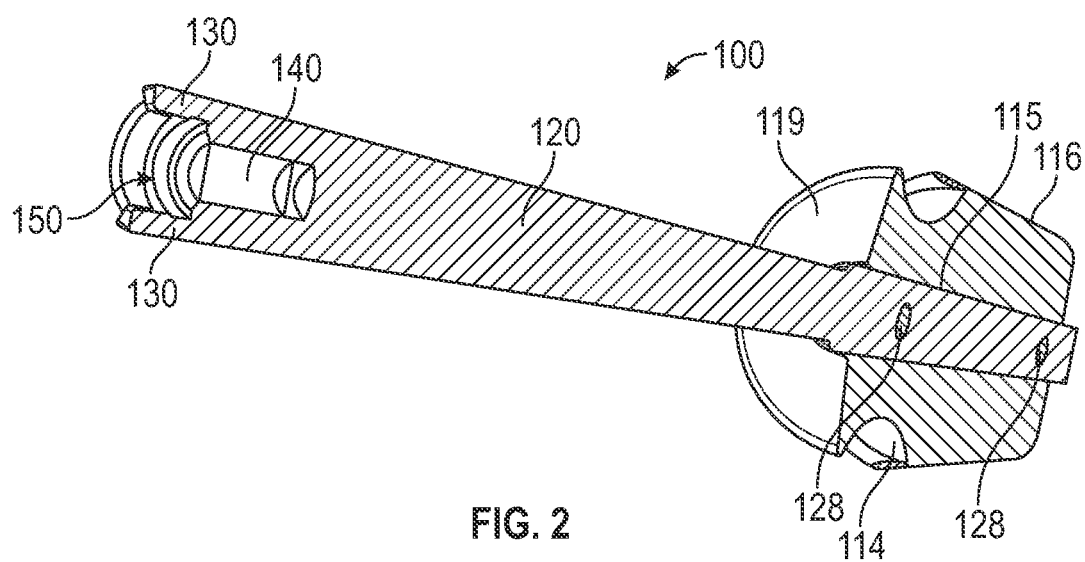
FIG. 2 shows a cross-sectional view of the first embodiment of multi-functional implant removal tool.

As seen in the cross-sectional view of FIG. 2, in some embodiments, handle 110 may be mounted to shaft 120, such as at proximal end 118 and distal end 119 by a friction fit, adhesive, or other mechanical mounting means. In some embodiments, proximal end 118 and distal end 119 may present substantially flat faces extending axially from the shaft 120. In some embodiments, handle 110 may have a length of about 110 mm to about 130 mm. In some embodiments, handle 110 may have a length of about 118 mm. In some embodiments, proximal handle portion 112 and distal handle portion 114 may form a unitary handle and may be constructed of a single material. Exemplary materials for handle 110 may include flexible or cushioned materials, such as rubber or plastic to provide a comfort grip to a user, or rigid materials such as metal, or other sterilizable materials. In some embodiments, handle 110 and/or shaft 120 may be configured as a slap hammer.

Shaft 120 includes proximal end 122, distal end 124, and central portion 126. Shaft 120 extends through central lumen 115 of handle 110. Proximal end 122 of shaft 120 may extend from the proximal end 118 of handle 110. Proximal end 122 of shaft 120 may be configured to connect to other handles or instruments as desired. Shaft 120 may include axial holes 128 therethrough within the portion located within the handle 110, which may receive fasteners for mounting therein. In some embodiments, axial holes 128 in combination with fasteners may be configured to transmit torque from handle 110 to shaft 120. In some embodiments, axial holes 128 may receive fasteners therein to mechanically fasten handle 110 to shaft 120. In some embodiments, two axial holes 128 may be spaced apart about 70 mm to about 90 mm. In some embodiments, shaft 120 may have a total length of about 230 mm to about 250 mm. In some embodiments, shaft 120 may have a total length of about 243 mm. In some embodiments, distal end 124 of shaft 120 has a diameter of about 5-7 mm. In some embodiments, distal end 124 of shaft 120 has a diameter of about 6.2 mm.

Figure 3:
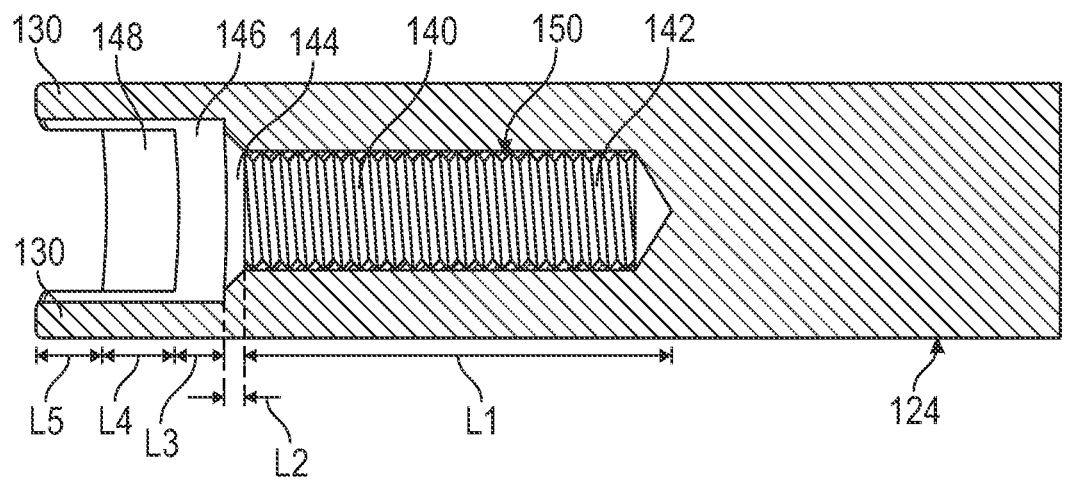
FIG. 3 shows a magnified cross-sectional view of the distal end of the first embodiment of multi-functional implant removal tool.
Figure 4:
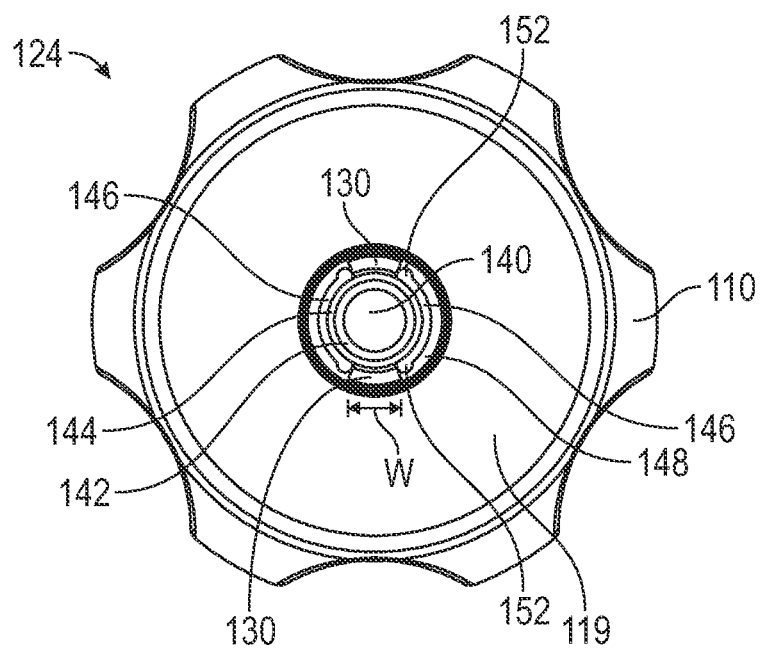
FIG. 4 shows a distal end view of the first embodiment of multi-functional implant removal tool.

FIG. 3 shows a magnified view of distal end 124 of shaft 120 and FIG. 4 shows a distal end view of tool 100. Distal end 124 is designed for cooperating with an implant, such as implant 200, specifically for insertion and/or removal thereof. In some embodiments, distal end 124 includes two tabs 130 extending a length L5 of about 1-5 mm from the distalmost end. In some embodiments, tabs 130 extend a length L5 of about 2 mm to about 4 mm. In some embodiments, tabs 130 extend a length L5 of about 3 mm. The tabs 130 each have a width w of about 2-3 mm around the circumference of the shaft 120. In some embodiments, the tabs 130 each extend around the circumference a distance W of about 2.9 mm to about 2.3 mm. In some embodiments, the tabs 130 each extend around the circumference a distance W of about 2.63 mm. In some embodiments, the tabs 130 each span an arc of about 40 degrees to about 60 degrees, as seen in FIG. 4. In some embodiments, the tabs 130 each span an arc of about 50 degrees. In some embodiments, the two tabs 130 are directly opposed to one another, thus they may be spaced about 130 degrees apart, as seen in FIG. 4. In some embodiments, tabs 130 have a substantially blunt, non-pointed distal end, as seen in FIG. 3. In some embodiments, tabs 130 may have a non-blunt distal end. Tabs 130 may have a wall thickness of about 1.6 mm to about 2.00 mm. In some embodiments, tabs 130 may have a wall thickness of about 1.8 mm.

The distal end 124 further includes a central bore 140 extending a length of about 7-15 mm, not including the length of the tabs 130. In some embodiments, central bore 140 extends a length of about 11 mm, not including the length of tabs 130. Proximal end of central bore 140 may include a flat bottom or a pointed drill point. Central bore 140 has a smaller (first) diameter proximal section 142, an intermediate (second) diameter section 144 larger than the first diameter proximal sections 142, a larger (third) diameter section 146 larger than either of the first or second diameter sections 142, 144, and a distal section 148. In some embodiments, smaller diameter proximal section 142 may extend a length L1 of about 10 mm. In some embodiments, smaller diameter proximal section 142 may have a diameter of about 2.9 mm. In some embodiments, intermediate diameter section 144 may extend a length L2 of about 0.2 mm. In some embodiments, intermediate diameter section 144 may have a diameter of about 3-4 mm. In some embodiments, larger diameter section 146 may extend a length L3 of about 1.3 mm. In some embodiments, larger diameter section 146 may have a diameter of about 3.4 mm to about 4.4 mm. In some embodiments, distal section 148 may extend a length L4 of about 1.5 mm to about 2.0 mm. In some embodiments, distal section 148 may extend a length of about 1.85 mm. In some embodiments, distal section 148 and has a diameter of about 3.7 mm. In some embodiments, distal section 148 and/or larger diameter section 146 have a wall thickness of about 1.6 mm to about 2.00 mm. In some embodiments, distal section 148 and/or larger diameter section 146 have a wall thickness of about 1.6 mm to about 1.8 mm. In some embodiments, distal section 148 may include an indented channel 152 proximal to the tabs 130, as can be seen in FIG. 4. In some embodiments, indented channel 152 facilitates machining the internal geometry of shaft 120. In some embodiments, distal section 148 and/or larger diameter section 146 have a wall thickness that is less than the wall thickness of tabs 130.

Smaller diameter proximal section 142 includes threads 150, which may be helical threads or box threads. In some embodiments, the pitch of threads 150 may be from about 0.5 mm to about 1.5 mm. In some embodiments, the pitch of threads 150 may be about 0.6 mm. In some embodiments, the pitch of threads 150 may be matched to the pitch of the threads of the implant that is to be removed. In some embodiments, the depth of threads 150 may be from about 2.0 mm to about 0.5 mm. In some embodiments, the depth of threads 150 may be about 1.00 mm. In some embodiments, threads 150 may have a thread angle of about 10° to about 75°. In some embodiments, threads 150 may have a thread angle of about 60°. In some embodiments, each threaded section may have multiple portions having different dimensional parameters. In some embodiments, some or all of the smaller diameter proximal section 142 may have threads 150 with different dimensional parameters, such as pitch, depth, and angle.

Figure 5A:
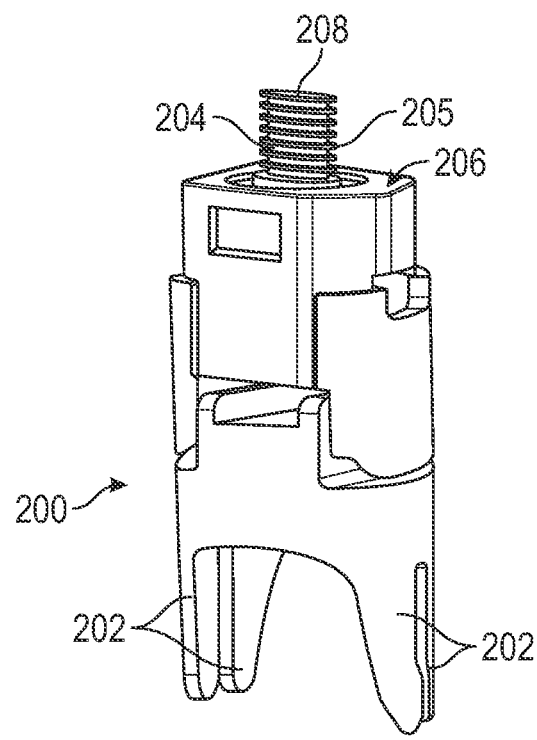
FIG. 5a shows an exemplary prior art implant in a closed position for implantation and removal.
Figure 5B:
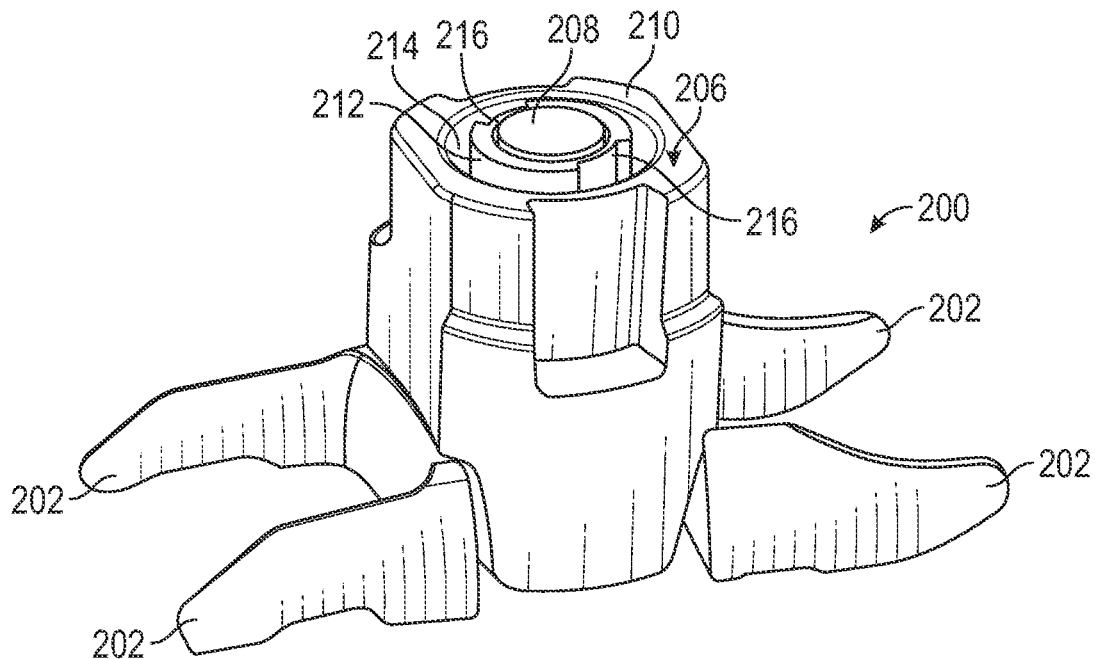
FIG. 5b shows the exemplary prior art implant in an open position for engaging a target site within the patient's body.

FIGS. 5a-5b show an exemplary known implant 200 that may be used together with the implant removal tool 100. Implant 200 may come in multiple sizes for fitting a particular patient's spine. In some embodiments, exemplary sizes for implant 200 may be 8 mm, 10 mm, 12 mm, 14 mm, or 16 mm. Implant 200 includes extendable wings 202, threaded internal shaft 204, and proximal face 206.

FIG. 5*a* shows the implant 200 in a closed position, where extendable wings 202 are folded, for implantation and removal. In the closed position, the extendable wings 202 are substantially aligned with the longitudinal axis of implant 200 and threaded internal shaft 204 extends a distance of about 6 mm to about 9 mm from the proximal face 206. Threaded internal shaft 204 includes proximal end 208 and external threads 205. External threads 205 may be helical threads or box threads. In some embodiments, the properties of external threads 205, such as the pitch, depth, angle, may be matched to the pitch of the threads 150 of implant removal tool 100 that is to be used. In some embodiments, each threaded section may have multiple portions having different dimensional parameters. In some embodiments, some or all of the threaded internal shaft 204 may have external threads 205 with different dimensional parameters, such as pitch, depth, and angle.

FIG. 5*b* shows the implant 200 in an open position, where the extendable wings 202 of the implant 200 are extended for engaging the target site within the patient's body. During initial implantation of the implant 200, threaded internal shaft 204, which initially extends from the proximal face 206 of implant 200, is configured to be rotated clockwise by a driver or introducer. This clockwise rotation moves the threaded internal shaft 204 distally along the longitudinal axis and expands the extendable wings 202 to the open position, as seen in FIG. 5*b*. Thus, once implant 200 is positioned in the patient, the threaded internal shaft 204 has been advanced within the interior of the implant 200 and the proximal end 208 of the threaded internal shaft 204 is almost flush with the proximal face 206 of the implant 200. In some embodiments, proximal end 208 of threaded internal shaft 204 extends a distance of about 6 mm to about 9 mm from the proximal face 206 of implant 200 in the open position, as seen in FIG. 5*b*. Proximal face 206 of implant 200 includes outer wall 210, collar 212 surrounding threaded internal shaft 204, and circumferential gap 214 therebetween. In some embodiments, circumferential gap 214 is greater than 0.5 mm wide. In some embodiments, circumferential gap 214 may be about 0.5 mm wide to about 2.0 mm wide. Collar 212 may further include two indented portions 216 around the circumference.

Figure 6:
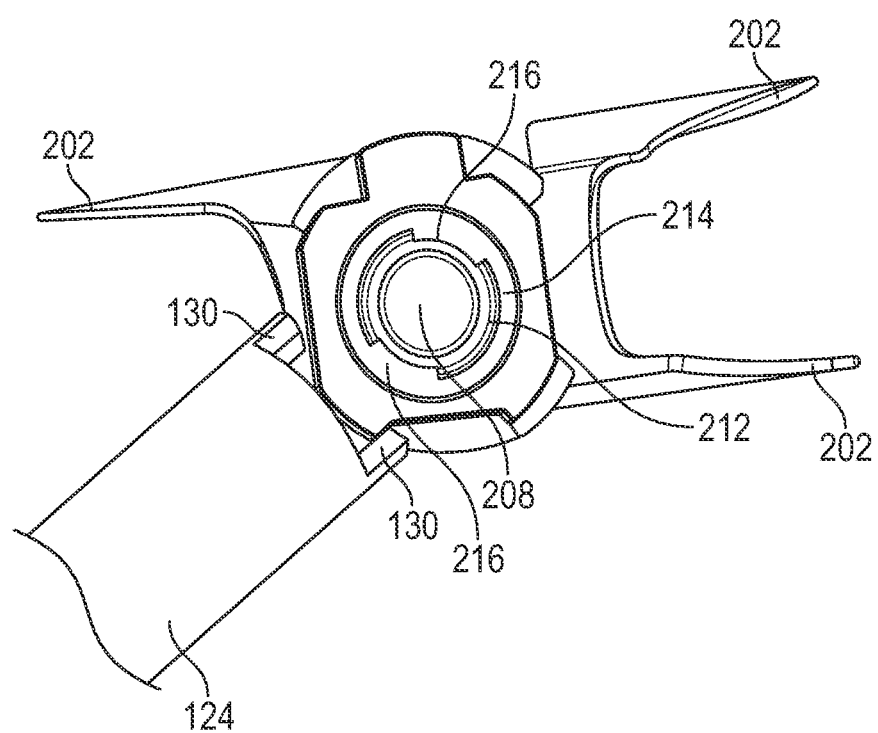
FIG. 6 is a perspective view of the exemplary prior art implant and the first embodiment of multi-functional implant removal tool.

As seen in FIG. 6, in order to remove the implant 200 after implantation, implant removal tool 100 may be engaged with the proximal face 206 of implant 200. Specifically, distal end 124 of implant removal tool 100 can be received within the circumferential gap 214. Tabs 130 may be about 0.9 mm thick, such that tabs 130 of tool 100 may fit within and engage indented portions 216 of collar 212. Distal end 124 may be about 0.5 mm thick, such that distal end 124 is sized to fit into circumferential gap 214.

Once tabs 130 are inserted into the indented portion 216 and distal end 124 is inserted into circumferential gap 214, the shaft 120 can be rotated counterclockwise. As the shaft 120 rotates, it turns the collar 212 and the threaded internal shaft 204 of the implant 200 due to the engagement of tabs 130 with indented portions 216. This counterclockwise rotation moves the threaded internal shaft 204 proximally along the longitudinal axis and moves the extendable wings 202 to the closed position, as seen in FIG. 5*a*. As the threaded internal shaft 204 extends from the proximal end 208 of the implant 200, it extends into the central bore 140 and engages the internal wall of the distal end 124. Specifically, the external threads 205 engage the threads 150 of smaller diameter proximal section 142 of shaft 120. In some embodiments, external threads 205 and proximal end 208 are received within shaft 120 a distance of about 10 mm to about 13 mm. Thus, the implant 200 can be locked onto the distal end 124 of shaft 120. Once the implant 200 is in a fully closed position, the shaft 120 can be retracted proximally from the implantation site, thus easily removing the implant 200 without having to use an additional tool. The single implant removal tool 100 allows for both closure of the wings 202 and locked engagement with the implant to withdraw the implant 200 from the site.

In some embodiments, all or part of the tool 100 may be composed of titanium or a titanium alloy. In other embodiments, all or part of the tool 100 may be composed of stainless steel. In some embodiments, all or part of the tool 100 may be composed of a polymer or a bioabsorbable material. In some embodiments the shaft may be composed of a material that is radiopaque or radiolucent. In some embodiments, the instrument may be manufactured by an additive manufacturing process. In some embodiments, the instrument may be manufactured by machining or molding.

Features described above as well as those claimed below may be combined in various ways without departing from the scope hereof. The following examples illustrate some possible, non-limiting combinations:

(A1) A surgical tool for removing a surgical implant including: a handle; a shaft mechanically coupled to the handle at a proximal end, the shaft having a distal end with a first wall thickness; the distal end including a central bore, the central bore having a proximal region including an internal threaded wall, the internal threaded wall is configured to receive a threaded shaft of an implant to be removed; and a plurality of tabs extending from a distalmost region of the central bore, the plurality of tabs having a second wall thickness greater than the first wall thickness such that the plurality of tabs extend radially into the central bore.

(A2) For the surgical tool denoted as (A1), the central bore includes: the proximal region having a first diameter; an intermediate region having a second diameter; and the distalmost region having a third diameter, the first diameter is smaller than the second diameter, and the second diameter is smaller than the third diameter.

(A3) For the surgical tool denoted as (A1) or (A2), the third diameter is about 3.4 mm to about 4.4 mm.

(A4) For the surgical tool denoted as any of (A1) through (A3), the plurality of tabs includes two curved tabs each having a blunt distal end.

(A5) For the surgical tool denoted as any of (A1) through (A4), the plurality of tabs includes two curved tabs each having a width around a circumference of about 2.3 mm to about 2.9 mm.

(A6) For the surgical tool denoted as any of (A1) through (A5), the plurality of tabs each extend longitudinally a distance of about 3 mm from the distalmost region.

(A7) For the surgical tool denoted as any of (A1) through (A6), the plurality of tabs each span an arc of about 40 degrees to about 60 degrees.

(A8) For the surgical tool denoted as any of (A1) through (A7), the internal threaded wall includes a plurality of helical threads having a pitch of about 0.6 mm.

(B1) A method of removing a surgical implant from a patient including: providing a removal tool including: a handle; a shaft extending from the handle, the shaft having a distal end with a first wall thickness; the distal end including a central bore, the central bore having a proximal region including an internal threaded wall; and a plurality of tabs extending from a distalmost region of the central bore, the plurality of tabs having a second wall thickness greater than the first wall thickness such that the plurality of tabs extend radially into the central bore; engaging the removal tool with an implant; and rotating the removal tool to lock the implant onto the distal end of the shaft.

(B2) For the method denoted as (B1), engaging the removal tool with the implant includes: inserting the plurality of tabs into a proximal face of the implant.

(B3) For the method denoted as (B1) or (B2), further including receiving the plurality of tabs in indented portions of a collar on the implant.

(B4) For the method denoted as any of (B1) through (B3), engaging the removal tool with the implant includes: inserting the distal end of the shaft into a circumferential gap on a proximal face of the implant.

(B5) For the method denoted as any of (B1) through (B4), further including: rotating the removal tool counterclockwise to engage a threaded shaft of the implant with the internal threaded wall.

(B6) For the method denoted as any of (B1) through (B5), rotating the removal tool counterclockwise further rotates the threaded shaft of the implant to close a plurality of wings of the implant.

(B7) For the method denoted as any of (B1) through (B6), further including: after locking the implant onto the distal end of the shaft, withdrawing the removal tool from a patient's body to remove the implant.

(C1) A surgical implant removal device including: a shaft having a proximal end and a distal end with a first wall thickness; the distal end including a central bore with a diameter of about 3.4 mm to about 4.4 mm; the central bore having a plurality of threads on an interior wall of the central bore; and two curved tabs extending from a distalmost region of the central bore, the two curved tabs having a blunt distal end, and the two curved tabs configured to cooperate with an implant for removal from a target site.

(C2) For the surgical implant removal device denoted as (C1), the plurality of threads are configured to cooperate with a threaded shaft of the implant.

(C3) For the surgical implant removal device denoted as (C1) or (C2), the central bore is sized to receive the threaded shaft of the implant.

(C4) For the surgical implant removal device denoted as any of (C1) through (C3), the two curved tabs each extend around a circumference a distance of about 2-3 mm and extend a length from the distal end of about 2-4 mm.

(C5) For the surgical implant removal device denoted as any of (C1) through (C4), the two curved tabs have a second wall thickness greater than the first wall thickness such that the two curved tabs extend radially into the central bore.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A surgical tool for inserting or removing a surgical implant, comprising:
   a handle comprising a handle distal end and a handle proximal end; and
   a shaft coupled to the handle, the shaft comprising:
      a shaft proximal end for coupling the shaft to a surgical instrument; and
      a shaft distal end extending from the handle distal end, the shaft distal end comprising:
         a first bore along a longitudinal axis, comprising:
            a proximal region having an internal threaded wall configured to receive a threaded shaft of the surgical implant, the proximal region defining a first diameter;
            a distal region; and
            an intermediate region between the proximal region and the distal region, the intermediate region defining a second diameter, at least two curved tabs disposed in the distal region, each of the at least two curved tabs extending radially into the first bore and having a blunt distal end,
   wherein each of the least two curved tabs is configured to engage a collar at a proximal face of the surgical implant.

2. The surgical tool of claim 1,
   wherein the distal region comprises a third diameter, and
   wherein the first diameter is smaller than the second diameter and the second diameter is smaller than the third diameter.

3. The surgical tool of claim 1, wherein the shaft proximal end extends from the handle proximal end.

4. The surgical tool of claim 1,
   wherein the handle further comprises a second bore along the longitudinal axis, and
   wherein the shaft further comprises a plurality of axial holes configured to receive a corresponding plurality of fasteners disposed along a length of the second bore to couple the shaft to the handle.

5. The surgical tool of claim 1, wherein each of the at least two curved tabs extends longitudinally about 3 mm from the distal region.

6. The surgical tool of claim 1, further comprising an indented channel disposed proximally from the at least two curved tabs.

7. The surgical tool of claim 6, wherein the indented channel is configured to facilitate machining of the at least two curved tabs.

8. A method of inserting or removing a surgical implant from a patient, comprising:
   providing a surgical tool having a length along a longitudinal axis, comprising:
      a handle comprising a handle distal end and a handle proximal end; and
      a shaft coupled to the handle, the shaft comprising a shaft proximal end extending from the handle proximal end and a shaft distal end extending from the handle distal end,
      wherein the shaft proximal end is configured to couple the shaft to a surgical instrument,
      wherein the shaft distal end comprises:
         a bore along the longitudinal axis, comprising:
            a proximal region having an internal threaded wall, the proximal region defining a first diameter;
            a distal region comprising at least two curved tabs each having a blunt distal end and extending radially into the bore; and
            an intermediate region between the proximal region and the distal region, the intermediate region defining a second diameter;

engaging the surgical tool with the surgical implant; and
rotating the surgical tool to lock the surgical implant onto the shaft distal end.

9. The method of claim 8, wherein engaging the surgical tool with the surgical implant further comprises coupling the internal threaded wall to a threaded shaft of the surgical implant.

10. The method of claim 9,
wherein engaging the surgical tool with the surgical implant further comprises inserting the at least two curved tabs into a proximal face of the surgical implant.

11. The method of claim 8, further comprising retracting the surgical tool proximally to remove the surgical implant from an implantation site.

12. The method of claim 8, wherein rotating the surgical tool further transitions the surgical implant from an open position to a closed position.

13. A surgical tool for inserting or removing a surgical implant, comprising:
a shaft comprising a distal end and a proximal end for coupling the shaft to a surgical instrument,
wherein the distal end comprises:
a first bore, comprising:
a proximal region having an internal threaded wall configured to receive a threaded shaft of the surgical implant, the proximal region defining a first diameter;
a distal region defining a second diameter; and
an intermediate region between the proximal region and the distal region, the intermediate region defining a third diameter; and
at least two curved tabs disposed in the distal region, each of the at least two curved tabs extending radially into the first bore and comprising a blunt distal end; and
wherein each of the at least two curved tabs is configured to engage a collar at a proximal face of the surgical implant.

14. The surgical tool of claim 13, further comprising:
a handle comprising a handle distal end, a handle proximal end, and a second bore extending between the handle distal end and the handle proximal end.

15. The surgical tool of claim 14, wherein the proximal end of the shaft extends from the handle proximal end.

16. The surgical tool of claim 14, wherein the shaft is at least partially received within the second bore.

17. The surgical tool of claim 14, wherein the shaft further comprises a plurality of axial holes configured to receive a corresponding plurality of fasteners to couple the shaft to the handle.

18. The surgical tool of claim 13, wherein the first diameter is smaller than the third diameter, and the third diameter is smaller than the second diameter.

19. The surgical tool of claim 13, wherein the distal region of the first bore defines a first wall thickness.

20. The surgical tool of claim 19, wherein each of the at least two curved tabs has a second wall thickness greater than the first wall thickness.

* * * * *